United States Patent [19]

Maines

[11] 4,279,506
[45] Jul. 21, 1981

[54] PHOTOMETRIC APPARATUS AND METHODS FOR COUNTING THE PARTICULATE COMPONENTS OF BLOOD

[75] Inventor: Robert Q. Maines, Tappan, N.Y.

[73] Assignee: R. J. Harvey Instruments Corp., Hillsdale, N.J.

[21] Appl. No.: 76,222

[22] Filed: Sep. 17, 1979

Related U.S. Application Data

[63] Continuation of Ser. No. 848,272, Nov. 3, 1977, abandoned.

[51] Int. Cl.³ .................... G01N 21/64; G01N 33/48
[52] U.S. Cl. ..................................... 356/39; 250/458; 356/244; 350/1.1
[58] Field of Search ........................ 356/39, 40, 41, 73, 356/244; 250/458

[56] References Cited

U.S. PATENT DOCUMENTS

| | | | |
|---|---|---|---|
| 2,959,665 | 11/1960 | Rhees | 356/40 |
| 3,358,148 | 12/1967 | Conklin et al. | 356/341 |
| 3,441,352 | 4/1969 | Hughes | 356/39 |
| 3,810,695 | 5/1974 | Shea | 356/73 |
| 3,847,482 | 11/1974 | Sokol et al. | 356/244 |
| 4,101,276 | 7/1978 | Anderson | 356/39 |

Primary Examiner—Vincent P. McGraw

[57] ABSTRACT

Photometric apparatus, for counting the particulate components in blood and for determining the degree of particulate agglutination, which comprises a cuvette for holding a blood bearing solution and an absorbent well for holding the cuvette. The well has a passage to allow communication between the cuvette and a detector which is capable of detecting the response of the particulate material to stimulating radiation. The absorbtive well has the characteristic of absorbing radiation at the wavelength which characterizes the response of the particulate material to stimulating radiation. The well advantageously prevents the detector from detecting radiation that would otherwise be reflected by the well whereby the linearity of the response of the apparatus is greatly increased. Linearity is further enhanced by assuring full crenation of the cells with a specific reagent.

7 Claims, 4 Drawing Figures

PHOTOMETRIC APPARATUS AND METHODS FOR COUNTING THE PARTICULATE COMPONENTS OF BLOOD

This is a continuation of application Ser. No. 848,272, filed Nov. 3, 1977, now abandoned.

FIELD OF THE INVENTION

This invention relates to quantizing the characteristics of various whole blood components, and more particularly this invention relates to determining the cell concentration in whole blood and to determining the degree of red blood cell agglutination.

BACKGROUND OF THE INVENTION

Commercially available automated equipment currently exists for analyzing the particulate or cell concentration in blood. This equipment measures either the interaction of the blood particles with electric fields or the interaction of the blood particles with visible radiation. Instruments which utilize electric fields for blood analysis require rather complex equipment while instruments utilizing optical analysis techniques are simpler. However, the simplicity found with optical instruments is frequently obtained at the expense of accuracy.

A disadvantage of utilizing optical equipment to analyze the particulate concentration in blood is the fact that the visible radiation intensity used to determine particulate concentration, does not vary linearly with changes in particulate concentration. This is due to the fact that instruments using nephelometric and/or turbinometric phenomenon have non-linear characteristics as a result of random scattering of light. The non-linear response of the optical equipment to the particulate concentration makes the interpretation of the output data difficult and somewhat inaccurate. If instrumentation is added to the optical equipment to linearize its response the simplicity of the optical equipment rapidly approaches that of the electric field instruments. Thus, a highly desirable goal in blood analysis is to develop a simple optical instrument, not requiring elaborate instrumentation, which responds linearly to changes in particulate concentration.

It is therefore, an object of this invention to provide simple optical equipment for automatically analyzing the particulate content in blood bearing solutions.

It is another object of this invention to provide optical equipment capable of simultaneously analyzing and detecting two constituents in blood bearing solutions.

It is a further object of this invention to provide an instrument capable of obtaining a linear reading of the degree of agglutination of red blood cells.

A still further object of this invention is to provide a technique for increasing the linearity of response of optical equipment used to determine the particulate concentration in whole blood and in other solutions.

SUMMARY OF THE INVENTION

In accordance with one aspect of the invention the particulate components in whole blood are counted and the degree of agglutination is determined by apparatus which detects the concentration or rate of change of concentration of particles, and/or other material, exhibiting a visible spectrum response to interactive radiation. The interactive radiation may be visible light, or radiation from radioactive sources, and may either be externally or internally generated. A transparent envelope containing a blood bearing solution is subjected to the interactive radiation and the envelope is surrounded by a broadly absorbent body having a central internal cavity accomodating and supporting the transparent envelope. The broadly absorbent body has a relatively restrictive passage allowing visual communication between the internal cavity and the exterior thereof. A detector having an electrical signal output and capable of detecting at least a portion of the responsive visible radiation spectrum is positioned to detect the responsive radiation communicated via the relatively restrictive passage.

It is a feature of the invention that the broadly absorbent body strongly absorbs radiation at the responsive visible radiation wavelength thereby eliminating the effects of radiation scattering from the wall of the well and advantageously increasing the linearity of the detector response.

In accordance with a second aspect of the invention multiple externally generated radiation sources are utilized to achieve simultaneous visible spectrum responses from at least two components of the blood. A transparent envelope contains the solution bearing the particulate components of blood and this envelope is surrounded by a broadly absorbent body having an internal cavity of size sufficient to accommodate and support the envelope. The broadly absorbent body has four coplanar relatively restrictive passages communicating between the internal cavity of the body and the exterior thereof. First and second passages have aligned axes extending in opposite directions from the cavity and third and fourth passages have aligned axes coplanar with said first and second passages which also extending in opposite directions from the cavity. Located externally to the body are two detectors with electrical signal outputs, a first of which is positioned to receive radiation via the second passage while a second detector is positioned to receive radiation via the fourth passage, each detector capable of detecting at least a portion of the responsive radiation spectrum.

It is another feature of the invention that each particle to be counted absorbs and/or scatters radiation at the wavelength of only one of the external radiation sources and each detector is responsive to only one of the external radiation sources whereby each detector measures the concentration of a particular particle.

In accordance with a third aspect and feature of the invention linearity and stability of response of visible radiation to the particle concentration in whole blood is enhanced by crenating the red blood cells with a specific reagent and by refractively matching the red cell membranes to the reagent.

The foregoing and other objects and features of this invention will be more fully understood from the following description of an illustrated embodiment thereof taken in conjunction with the accompanying drawings.

DETAILED DESCRIPTION

Figure 1:
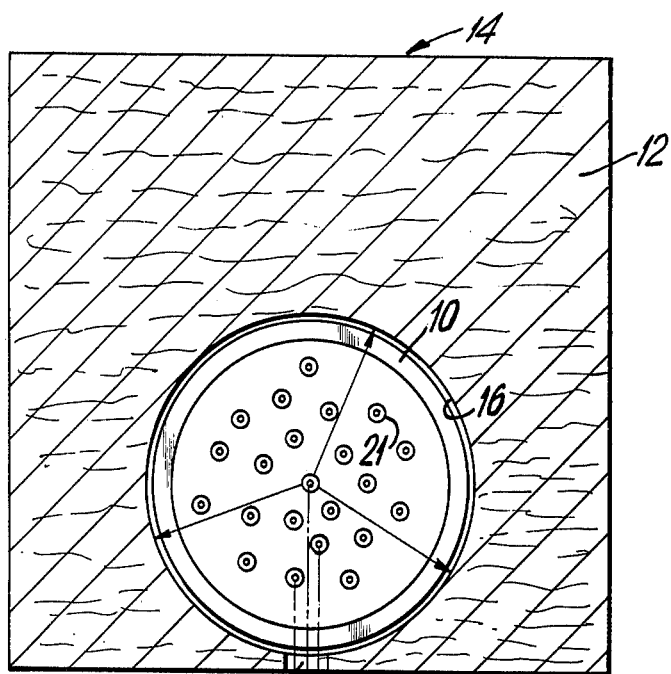
FIG. 1 is a top sectional view of a counting chamber where the detected radiation results from radioactive decay of isotopes added to the solution.

Refer to FIG. 1. Therein is shown a first embodiment of the invention. A transparent cuvette or envelope 10 is surrounded with and supported by a rectangular body or well 12, the well having an exterior surface 14 and a centrally located internal cavity 16. The internal cavity 16 is carefully sized such that it is large enough to accommodate the envelope 10 but small enough to provide adequate support therefor. Rectangular body or well 12 has a relatively restrictive passage 18 communicating between the internal cavity 16 and the exterior surface 14 of the rectangular body or well 12. A photomultiplier detector 20 is positioned to intersect the path of the relatively restrictive passage thereby receiving any radiation transmitted via the restrictive passage 18.

A measured quantity of liquid, including material which contains a radioactive isotope such as $C_{14}$, is placed in the cuvette 10. Also included in the liquid is material capable of fluorescence in response to the radioactive isotope. The $C_{14}$ generates a characteristic radiation which excites the fluoresce material in the liquid and causes it to fluoresce at wavelengths between 380 and 420 nm. This radiation is transmitted via the relatively restrictive passage 18 to photomultiplier detector 20. Detector 20 detects the radiation generated by the particles in the solution and, in response thereto, the detector produces an electrical output signal. The magnitude of the electrical output signal is proportional to the concentration of $C_{14}$ and also is proportional to the concentration of the material containing $C_{14}$, and this signal output can be utilized in a well known manner to operate display devices for indicating the material concentration. The material can be red blood cells or any other organic material capable of being tagged with $C_{14}$.

The material contained within the cuvette 10 such as material 21 is not limited to cell particles but is meant to indicate any material containing $C_{14}$ which excites the fluorescent material in the liquid.

An important aspect of the invention is the fact that broadly absorbent well 12 is advantageously constructed of a material which when dyed, will strongly absorb radiation in the wavelengths from 340 to 640 nm. Therefore, all radiation sensed by detector 20 consists of radiation generated by the excited material in the liquid and does not consist of secondary radiation caused by reflection of the transmitted radiation from the sides of well 12. The lack of reflected radiation is due to the fact well 12 has been constructed of a material which strongly absorbs radiation at the wavelength of the radiation being generated by the excited material. This is in marked contrast to prior art devices which utilize a non-absorbent well thus causing scattering of the generated radiation. This scattering or reflection off the walls of the well results in the detector response being partially due to a reflected component of radiation, thereby causing undesirable non-linearly in the detector output. Using an absorbent well having an absorption band that matches the wavelength of the light sensed by the detector ensures that the resulting detector response will entirely be a function of the first order light generated by the excited material and thus the detector output signal will vary linearly with $C_{14}$ concentration.

A well 12, broadly absorbent of radiation, can be made from a cast or molded of a material such as Nylon IV which can be produced in accordance with the teachings set forth in U.S. Pat. Nos. 3,174,951 and 3,721,625. Nylon IV can be dyed with commercially available dyes to make Nylon IV strongly absorbent of radiation across the entire visible spectrum and the ultra-violet spectrum. More particularly, to make Nylon IV strongly absorbent across a broad range of wavelengths the Nylon IV can be dyed with commercially available dyes obtainable from Crompton and Knowles Corporation of Reading, Pennsylvania or Barson Corporation of Stamford, Connecticut. Examples of dyes utilized to make the Nylon IV absorbent from 340 nm to 640 nm include the following, Altco Fast Black, Super Nylite Black 40R, Intralow Black BGL, Nylonthrene Black GLRT, Azoanthrene Jet Black K, Direct Black E and Intrachrome Black WA.

Procedures recommended by Crompton and Knowles and/or Barson are utilized to dye the Nylon IV. These dying procedures are supplied by Crompton and Knowles and/or Barson along with the appropriate dyes. Dying the Nylon IV well material in accordance with these teachings ensures that the well material will be strongly absorbent at the visible and ultra-violet wavelengths and thus all radiation collected by detector 20 will be radiation stemming from the excited particles in the solution and will not be radiation reflected from the walls of well 12.

Figure 2:
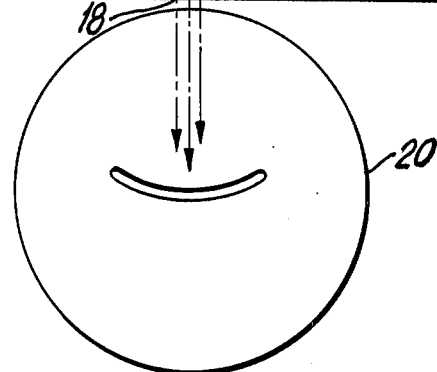
FIG. 2 is a top sectional view of a counting chamber where the incident radiation is generated by a single monochromatic external source and the measured radiation is the transmitted radiation.
Figure 2:
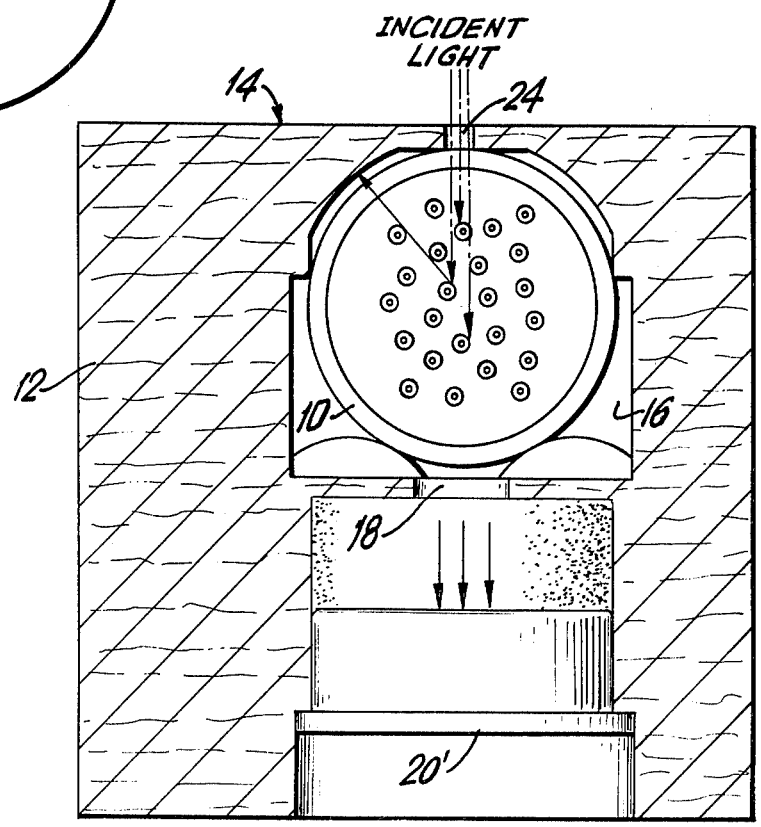

FIG. 2 illustrates a second embodiment of the invention. The apparatus shown therein consists of a transparent cuvette or envelope 10 surrounded by a rectangular body or well 12, having an exterior surface 14 and a centrally located internal cavity 16. The central cavity 16 is carefully sized such that it is large enough to accommodate the envelope 10 but small enough to provide adequate support for the envelope 10. The well 12 of the present embodiment differs from the first embodiment in that it has two relatively restrictive passages rather than one relatively restrictive passage. The first relatively restrictive passage 24 communicates between the internal cavity 16 and the exterior surface 14 of the rectangular body or well 12. A second relatively restrictive passage 18 having a common axis with the first relatively restrictive passage 18 extends in the opposite direction from the central cavity 16 and communicates between the central cavity 16 and the surface 14.

Adjacent to exterior surface 14 of well 12 is a solid state detector 20' which is positioned to intersect the path of the first relatively restrictive passage 18 and is positioned so as to detect radiation transmitted through passage 18. Such solid state detectors are commercially available and could, for example, be a Hammatmatsu silicon photo-cell detector.

In this embodiment of the invention a measured quantity of a blood bearing solution having the particulate component randomly dispersed throughout is placed in the cuvette 10. An externally generated monochromatic light of a wavelength equal to 540 or 578 nm is directed into the cavity via the second relatively restrictive passage 24. The monochromatic light passes through the cell membrane and is strongly absorbed by the oxyhemoglobin in the red cell and the number of particles in the light path is then directly proportional to the amount of light absorbed. The light transmitted through the solution is directed to solid states detector 20' via relatively restrictive passage 18. The intensity of the radiation received by detector 20' decreases as the concentration of the particles increases. Therefore, the detector output can readily be utilized to operate display devices for indicating the cell concentration of cells in whole blood.

Determining the concentration of cells in whole blood through use of an external radiation source as in FIG. 2 requires an additional consideration due to the shape of the cells. More particularly, blood cells are rather flat, and transparent to light and thus their response to the incident light will depend on the orientation of each cell with respect to the axis of the transmitted light and will also depend on the swirling motion of the cells within the solution. A more linear detector response to the transmitted light can be obtained by first crenating the blood cells with the proper reagent. Full crenation of the cells is accomplished by adding about one part of whole blood to five hundred parts of a hypertonic solution which contains distilled water to which has been added about 3% by weight of Sodium Benzoate 6% by weight of dextran having an average molecular weight of about 200,000 to 300,000. The whole blood and the hypertonic solution are thoroughly mixed and the mixture is allowed to stand for a minimum of about one minute to ensure that the cells are fully crenated. A solution of the above composition, in addition to preparing the red blood cells by crenation, also serves to provide a solution which has an index of refraction which approximately matches the index of refraction of the red blood membrane and thus reduces the reflected light and enhances the linearity of the detector response. In addition, the effective total area of the concentrated red cell hemeprotein in the light path has to be small in comparison to the total area of the incident light beam. An appropriate ratio of hemeprotein area to light beam area is 1 to 10. Such a ratio is achieved by proper dilution of the solution and ensures that counting errors will not result as cell volume increases or decreases. This minimizes counting errors due to MCV (mean corpuscular volume) variations. This relationship must be utilized with the embodiment of FIG. 2 and the embodiment of FIG. 4 to be described hereinafter.

The body material of well 12 is again advantageously designed to be absorbent at the wavelength of the radiation transmitted by the external monochromatic light source. The specific material of which well 12 is constructed, and the manner in which this material is rendered absorbent at the wavelength of the monochromatic light source is in accordance with the teachings of U.S. Pat. Nos. 3,174,951 and 3,721,625 and the dying process described above. Since the body material of well 12 is adsorbent at the wavelength of the transmitted radiation the intensity of the measured radiation will vary linearly with respect to particle concentration and will not be affected by reflections from the walls of well 12 due to the fact that the well wall is absorbent.

Figure 3:
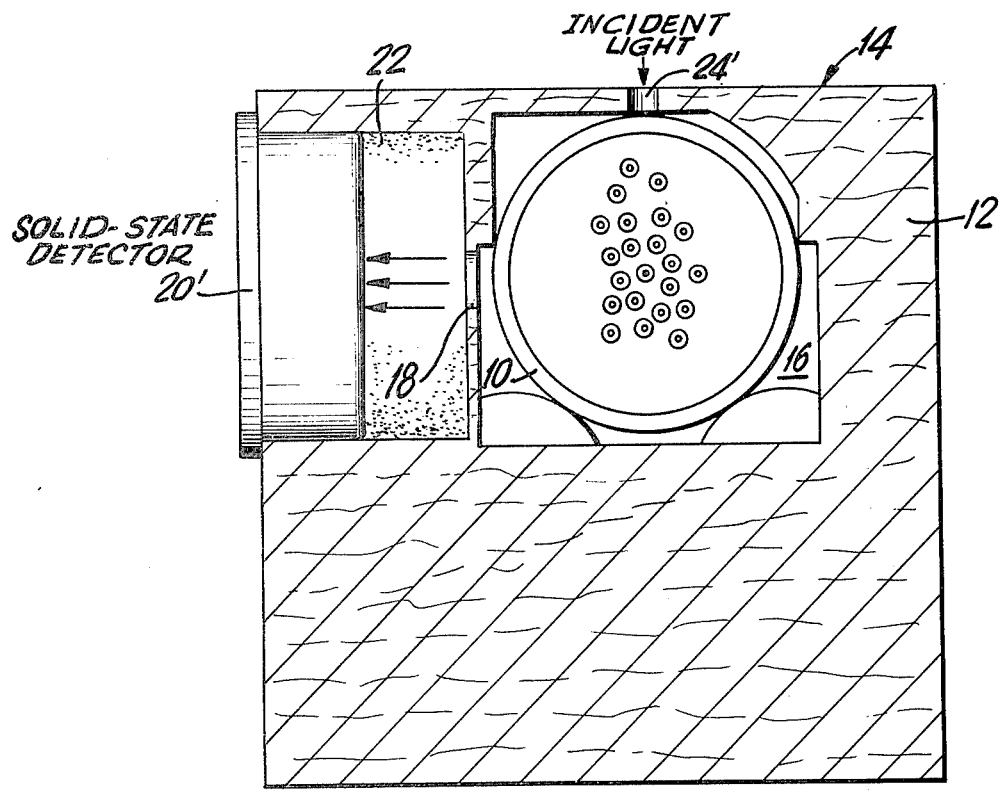
FIG. 3 is a top sectional view of a counting chamber where incident radiation from an external monochromatic source excites fluorescence by the particles, the fluorescence being measured.

FIG. 3 illustrates a third embodiment of the invention. The apparatus shown therein includes cuvette 10, internal body cavity 16, the selectively absorbent well 12 and an additional element not previously used, namely filter 22. This embodiment of the invention is contrasted with the previous embodiments in that the second relatively restrictive path 24' is perpendicular to the first relatively restrictive path 18 and extends from central cavity 16 to the surface 14. This apparatus is particularly well suited to an application wherein an externally generated monochromatic light source is employed to excite fluorescence in the species being studied. When employing a light source to excite fluorescence there is always the problem of having the detector differentiate between the light source and the radiation generated through fluorescence. Such differentiation is necessary if the detector output is to accurately reflect particle concentration. This problem is solved in the above described configuration of restrictive passages due to the fact that passage 24' is perpendicular to passage 18 thereby ensuring that the detector is shielded from the direct beam of the external monochromatic light source. This feature enhances the linearly of the detector response as all light incident on the detector is generated by the fluorescence originating from the solution. In addition, filters 22 are arranged to block radiation at the frequency of the incident light thereby adding to the accuracy of the concentration readings. Examples of radiation wavelengths are 366 nm for the wavelength of the incident light and 450 nm for the wavelength of fluorescence.

Again, the material of well 12 is advantageously made strongly absorbent at the wavelengths of the fluoresced light and the incident light. This further increases the linearity of the detector response in accordance with the teachings outlined above. In this configuration the well material can be made absorbent at the wavelength of both the fluoresced light and the external light but absorbence should principally occur at the wavelength of the fluoresced light.

Figure 4:
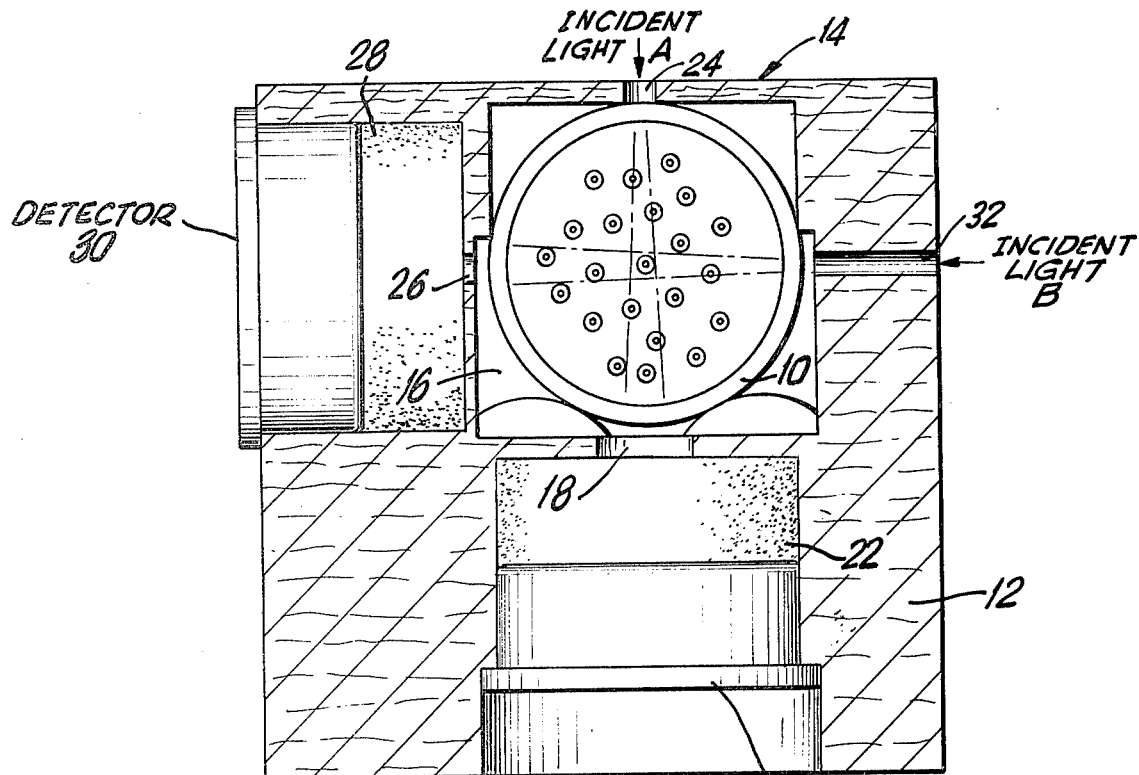
FIG. 4 is a top sectional view of a counting chamber where incident radiation is generated by two external monochromatic sources.

A fourth embodiment of the invention is shown in FIG. 4. This embodiment includes the structural elements defined above, namely, the absorbptive well 12, the cuvette 10, body cavity 16 and filters 22. This embodiment differs from those described above in that it has a second pair of relatively restrictive passages 26 and 32 communicating between the central cavity 16 and the surface 14 of the well 12. Associated with third relatively restrictive passage 26 is a second series of filters 28 and a second solid state detector 30. The spacial radiation between the second series of filters 28, the second solid state detector 30 and the third relatively restrictive passage 26 is the same as the spacial relation between the first series of filters 22, solid state detector 20', and the first relatively restrictive passage 18. The fourth relatively restrictive passage 32 directs a second externally generated monochromatic light source into the central cavity 16.

The apparatus in FIG. 4 allows the simultaneous measurement of the concentration of two species in whole blood. More particularly, the white blood cell concentration and the platelet concentration can be measured simultaneously. This is accomplished by setting the wavelength of incident light source A at 420 nm and the wavelength of incident light source B at 460 nm. When the blood bearing solution has been treated with the reagent described above in relation with the crenation process the platelets in the blood reflect light at 420 nm and are completely transparent to the light at 460 nm. Therefore, the light from source A (420 nm) will be reflected by the platelets and absorbed by the well and thus the output of detector 20' will reflect the platelet concentration. Similarly, the light from source B (460 nm) will be absorbed by the white blood cells and the output of detector 30 will reflect the white blood cell concentration. Filters 22 advantageously reject at 460 nm and filters 28 reject at 420 nm to further increase concentration measurement accuracy. Again, the material of well 12 is dyed in accordance with the teachings set forth above to be absorbent at 420 nm and 460 nm to thereby greatly increase the linearly and accuracy of the cell concentration readings.

All of the embodiments described above can also be used to determine the degree of agglutination of the red blood cells. More particularly, in accordance with the previous teachings it can be appreciated that the apparatus of the instant invention will provide an accurate reading of the number of red blood cells. As the red blood cells agglutinate together this count will decrease at a specific rate based on the number of cells that combine together. Due to the enhanced linearily inherent in the apparatus of the instant invention the degree of agglutination can be accurately determined.

Although the present invention has been described in conjunction with preferred embodiments; it is to be understood that modifications and variations may be resorted to without departing from the spirit and scope of the invention as those skilled in the art will readily understand. Such modifications and variations are considered to be within the purview and scope of the invention and the appended claims.

What is claimed is:

1. Photometric apparatus for determining particulate concentration in whole blood suspended in a liquid solution, said particulate having a visible radiation response to interactive radiation, the apparatus comprising, a transparent envelope for containment of a liquid solution having suspended therein particulate components of blood, a body having an internal cavity of sufficient size so as to surround and support said envelope, said body containing a relatively restrictive passage communication between the internal cavity of said body and the exterior surface of said body, said body having the characteristic of absorbing radiation at the wavelength of the visible radiation, and means positioned to intercept the visible radiation via said restrictive passage for detecting at least a portion of the radiation spectrum at the wavelength of the visible radiation, and for indicating particulate concentration in response thereto, said body being comprised of Nylon IV dyed to render said body absorbent of radiation across the entire visible and ultra-violet spectrum.

2. Photometric apparatus as recited in claim 1, wherein said restrictive passages includes two relatively restrictive apertures directly connecting the central cavity to the external surface of said body, one of said apertures directing externally generated radiation from a first source into said cavity, and the other of said apertures directing the particulate responsive visible radiation to the detection and indicating means.

3. Photometric apparatus as recited in claim 2, wherein said apertures have aligned axes extending in opposite directions from said cavity.

4. Photometric apparatus as recited in claim 2, wherein said restrictive passage includes third and fourth apertures having aligned axes extending in opposite directions from said cavity, said aligned axes of said third and fourth apertures being coplanar with the axes of the first and second apertures respectively, said third passage directing externally generated radiation from a second source into said cavity and, said fourth passage directing particulate responsive visible radiation from said cavity to second detection and indicating means.

5. Photometric apparatus as recited in claim 4, further including first and second filter means arranged in said second and fourth apertures respectively, said first filter means arranged to reject radiation at the wavelength of the first source and said second filter means arranged to reject radiation at the wavelength of the second source.

6. Photometric apparatus for counting the particulate components of blood suspended in a liquid solution, said particulate having a visible radiation response to interactive radiation, said apparatus comprising, a transparent envelope for containing a solution having suspended therein particulate components of blood, a body having an internal cavity of sufficient size so as to accommodate and support said envelope therein, said body having four coplanar relatively restrictive passages communicating between the internal cavity of said body and the exterior of said body, and having the characteristic of absorbing radiation at the wavelength of the visible radiation, first and second passage having aligned axes extending in opposite directions from said cavity, third and fourth passages having aligned axes coplanar with said first and second passages and extending in opposite directions from said cavity, a first detector positioned to receive radiation via said second passage, a second detector positioned to receive radiation via said fourth passage, said first passage directing into said cavity a first externally generally monochromatic radiation interactive with said particulate, the response of the particulate to said first radiation being detected by said first detector, and said third passage directing into said cavity a second externally generated monochromatic radiation interactive with said particulate, the response of the particulate to said second radiation being detected by said second detector, said body being comprised of Nylon IV dyed to render said body absorbent of radiation across the entire visible and ultra-violet spectrum.

7. Photometric apparatus for determining the concentration of a radioactive isotope such as $C_{14}$ suspended in a liquid solution, said solution also containing fluorescent material which has a visible radiation response to the radioactive isotope, the apparatus comprising a transparent envelope for containment of the liquid solution, a body having an internal cavity of sufficient size so as to surround and support said envelope, said body containing a relatively restrictive passage communicating between the internal cavity of said body and the exterior surface of said body, said body having the characteristic of absorbing radiation at the wavelength of the visible radiation, and means positioned to intercept the visible radiation via said restrictive passage for detecting at least a portion of the radiation spectrum at the wavelength of the visible radiation, and for indicating radioactive isotope concentration in response therein, said body being comprised of Nylon IV dyed to render said body absorbent of radiation across the entire visible and ultra-violet spectrum.

* * * * *